(12) United States Patent
Bernard et al.

(10) Patent No.: US 9,056,695 B2
(45) Date of Patent: Jun. 16, 2015

(54) CONNECTION OF AN ACCESSORY TO A RECEPTACLE

(75) Inventors: Frederic Bernard, La Cadiere d'Azur (FR); Sebastien Chaussin, Aubagne (FR); Jeremy Gibelin, Le Beausset (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 0 days.

(21) Appl. No.: 14/232,722

(22) PCT Filed: Jul. 12, 2012

(86) PCT No.: PCT/FR2012/051662
§ 371 (c)(1),
(2), (4) Date: Jan. 14, 2014

(87) PCT Pub. No.: WO2013/011231
PCT Pub. Date: Jan. 24, 2013

(65) Prior Publication Data
US 2014/0124504 A1    May 8, 2014

(30) Foreign Application Priority Data

Jul. 19, 2011 (FR) .................................. 11 56540

(51) Int. Cl.
| | | |
|---|---|---|
| B01L 99/00 | (2010.01) |
| B65D 25/00 | (2006.01) |
| A61M 39/18 | (2006.01) |
| C12M 3/00 | (2006.01) |
| A61J 1/20 | (2006.01) |
| A61J 1/14 | (2006.01) |

(52) U.S. Cl.
CPC ......... B65D 25/005 (2013.01); *Y10T 29/49826* (2015.01); *A61M 39/18* (2013.01); *C12M 23/46* (2013.01); *A61J 1/1475* (2013.01); *A61J 1/2093* (2013.01); *A61J 2001/2037* (2013.01); *A61J 2001/2051* (2013.01); *A61J 2001/2068* (2013.01)

(58) Field of Classification Search
CPC .................................. C12M 33/04; G01N 1/10
See application file for complete search history.

(56) References Cited

U.S. PATENT DOCUMENTS

| | | |
|---|---|---|
| 2005/0239198 A1 | 10/2005 | Kunas et al. |
| 2009/0178495 A1 | 7/2009 | Steigmiller et al. |
| 2010/0301060 A1 | 12/2010 | Bernard et al. |

FOREIGN PATENT DOCUMENTS

| | | |
|---|---|---|
| DE | 25 57 542 | 6/1977 |
| DE | 42 07 845 | 9/1993 |
| DE | 10 2004 015703 | 11/2005 |
| FR | 2 924 034 | 5/2009 |
| WO | 86/07151 | 12/1986 |
| WO | 2009/071829 | 6/2009 |

OTHER PUBLICATIONS

International Search Report dated Sep. 13, 2012, corresponding to PCT/FR2012/051662.

*Primary Examiner* — Jyoti Nagpaul
(74) *Attorney, Agent, or Firm* — Young & Thompson (57) ABSTRACT

The device (1) for the sealed connection to a receptacle (2) of an accessory (3), the active proximal part (9) of which is intended to be connected to the inside (4) of the receptacle (2) by an opening (7) in the receptacle (2), includes a first element (15), a second element (16) and a chamber (18), the first element (15) including a proximal end part (32) which is secured by sliding in the proximal direction, with insertion of a lateral sealing component (22), onto a matching part (19) of the receptacle (2), in the proximal direction, the transverse head (14) corresponding to the lower surface of the first element (15) and being provided with a lateral head sealing component (28) and the second element (16) being capable of being pre-assembled with the first element (15) by axial sliding in the proximal direction.

30 Claims, 2 Drawing Sheets

CONNECTION OF AN ACCESSORY TO A RECEPTACLE

The invention concerns an improvement to the connection of an accessory to a receptacle.

More specifically, a first object of the invention relates to a device for the connection to a receptacle of an accessory of which the active proximal part is intended to be placed in communication with the inside of the receptacle by an opening in the receptacle.

A second object relates to an assembly for measurement or monitoring of a parameter of a liquid contained inside a receptacle, by means of a measurement or monitoring accessory comprising said connection device.

A third object relates to an assembly with receptacle for biopharmaceutical applications with measurement or monitoring of a parameter of a liquid contained inside the receptacle, comprising such a connection device or such an assembly for measurement or monitoring.

A fourth object relates to a method for the pre-assembly of such an assembly for measurement or monitoring.

A fifth object relates to a method for mounting such an assembly with receptacle.

A sixth object relates to a method for making use of such an assembly for measurement or monitoring.

In this particular case, the receptacle in question is a receptacle for storing and/or processing content such as a biopharmaceutical product. The receptacle in this particular case is understood to mean a reusable rigid container or a flexible disposable container such as a bag.

This bag may be what is referred to as a 2D bag, such as the ones sold by Sartorius Stedim Biotech under the brand Flexboy®, having a typical volume of between 50 ml and 50 liters.

It is also possible for this bag to be a flexible container as described in WO 00/04131, whose volume can and usually does exceed 50 liters. Such a receptacle is commonly referred to as a 3D bag and is sold by Sartorius Stedim Biotech under the brand Flexel®. It is known to associate this bag with rigid external support means, at least when it is holding its content.

"Biopharmaceutical product" is understood here to mean one or more product(s) originating from biotechnology (culture media, cell cultures, buffer solutions, artificial nutrition liquids), or a pharmaceutical product, or more generally a product intended for use in the medical field. The product is liquid, pasty, or powdery, in one or more phases, possibly homogeneous, and able to flow through a valve, which is why the product can be considered a fluid in the context of the invention. The invention also applies to products other than biopharmaceutical products as just defined, but which are subject to similar requirements concerning storage or processing.

"Accessory" is understood here to mean a sensor for measuring parameters relating to the contents of the receptacle, such as pressure, pH, temperature, colorimetry, conductometry, etc., or even a supply tube or drainage tube. The invention also applies to other accessories which are connected to a receptacle by being placed in communication with the inside of said receptacle.

In the biopharmaceutical field, it is common to use these receptacles as a place for carrying out chemical or biological reactions, and possibly for monitoring and/or controlling these reactions, or as a storage means. To prevent germs from entering the receptacle, it is important that the environment be closed, sterile, and aseptic, with no contact with the external environment.

The reactions must generally take place under defined and monitored conditions (pressure, pH, temperature, colorimetry, conductometry, etc.), or the storage under controlled conditions. It is therefore necessary to measure or monitor the parameters characterizing the product contained in the receptacle on a more or less frequent basis. These measurements must be obtained under aseptic conditions, for the reasons stated above.

Document DE 10 2004 015703 discloses a connection device comprising two elements equipped with guide means and hooks.

DE 42 07 845 describes an analytical electrode holder, comprising a stationary outer tube, a slideable inner tube, and a transversely mounted assembly including a piston mounted in a housing, this assembly forming a fluid-tight entrance for the inner tube, to allow removing the electrode from the container in which it is intended to be placed, without losing the contents of said container.

WO 86/07 151 discloses a maintenance device for the automatic cleaning and calibration of a probe that is part of a system for continuous measurement of a chemical or biological process, consisting of analyzing the parameters of the fluid to be investigated.

Document DE 25 57 542 discloses a device for measuring electrical values of flowing media with measurement sensors arranged in passage enclosures, in which the passage of a valve housing forms the passage enclosure and the detector is mounted in said enclosure.

Document US2005/0239198 discloses a sterile and aseptic connection established by means of two elements, a first element fixed to the receptacle and a second element adapted for connection to the first element. The first element has, at its free end, a connecting means provided with a lid. The second element comprises a probe arranged within a flexible sleeve provided with a connection means provided with a lid, the connection means of the second element being intended for connection to the connection means of the first element after removal of the respective lid. The probe is attached to the receptacle by sliding the connection means of the second element into the connection means of the first element. The probe tip is then inserted into the receptacle by compression of the sleeve, the sensor sliding inside the first element until it reaches the inside of the receptacle.

Document US2009/0178495 discloses a sampling valve by which samples containing mechanically-sensitive materials are collected from a bioreactor in a sterile manner.

Document WO 2009/071829 discloses a device for connecting to a receptacle (referred to as a "vessel" in this patent) an accessory having an active proximal part adapted to be placed in communication with the inside of the receptacle via an opening of the receptacle, the device comprising a first member, a second member, a third member, and a chamber, wherein:

the function of the first member is to ensure the rigid attachment of the connection device to the receptacle, to define a passageway between the inside and the outside of the receptacle, to act as a holder for the second member and as an axial translation guide along an axial stroke C of which the two ends correspond to a distal first state and a proximal second state, to contribute as a guide for the third member, and to participate in the definition of the chamber, the function of the second member is to act as a holder for the third member which is rigidly attached thereon, to define a mobile element capable of sliding axially along the stroke C of which the two ends of the path correspond to the distal first state and the proximal second state, the function of the third member, which comprises a head, is to act as a holder for the accessory which is rigidly attached thereon, to define a movable member capable of sliding axially along the stroke C of which the two ends of the path correspond to the distal first state and the proximal second state, to ensure in the distal first state the fluid-tight closing of the opening by means of the head, to ensure in the proximal second state a protection of the active proximal part by means of the head, and to participate in the definition of the chamber, the chamber is closed and fluid-tight in the distal first state, and in the proximal second state it is in communication with the inside, and the function of the chamber is to house therein or to place at the periphery thereof the active proximal part, and where appropriate to contain a storage liquid, to contain a liquid for preserving, adjusting, monitoring, or calibrating the accessory, or to define a closed and fluid-tight chamber in which the accessory is placed while awaiting its use.

According to the detailed description of one particular embodiment of such a connection device, said device comprises, in addition to the accessory, three elements consisting of three separate parts assembled together. The part constituting the first element is tubular, with at one end a transverse annular flange intended to be attached directly to the wall of the receptacle, around its opening. The part constituting the third element comprises a head in the form of a transverse wall, the peripheral edge comprising a shoulder adapted to cooperate with the seating formed by the transverse flange of the first part, the head having a larger diameter than the opening of the receptacle.

With this particular embodiment, the method for mounting the connection device, the accessory, and the receptacle consists of the following operations:
- an empty receptacle, the accessory, and the component elements of the connection device are provided,
- the first element is rigidly attached to the receptacle at the opening,
- the accessory is inserted into the third element and is rigidly attached thereto,
- the assembly of the third element+accessory is assembled onto and into the second element,
- the assembly of the second element+third element+accessory is assembled onto and into the first element.

Such an assembly method, which is generally carried out in a clean room, therefore has the following and other drawbacks:
- such a connection device is mounted manually by an operator on the same production line as for said pharmaceutical receptacle, which directly impacts productivity.
- the accessory may require handling liquids, which in a clean room represents a high risk of contamination of the products produced. For example, if the accessory is a pH probe it will be necessary to fill the chamber with liquid to prevent the pH probe from drying.
- manipulation of the various elements and the possible manipulation of liquids make this a tedious assembly method for the operator.

The invention aims to improve the device for connection to a receptacle of an accessory of which the active proximal part is adapted to be placed in communication with the inside of the receptacle via an opening of the receptacle of the type taught by WO 2009/071829.

While retaining the advantages of such a device, the invention simplifies it, allows its pre-assembly and where appropriate the filling of its chamber outside a clean room, provides assembly and mounting by a simple axial sliding in the proximal direction, and guarantees a fluid-tight seal of the chamber so that it is possible to perform a new calibration of an accessory such as a probe while limiting the risk of contamination.

For this purpose, a first aspect of the invention relates to a device for the fluid-tight connection to a receptacle of an accessory of which the active proximal part is intended to be placed in communication with the inside of the receptacle by an opening in the receptacle, the device having an axis and comprising:
- a first means of generally tubular shape with a proximal end opening and a distal end opening, arranged to ensure the attachment of the device to the receptacle, to define a passageway between the inside and the outside of the receptacle, to form a support that guides the axial sliding of the second means between a closed distal state and an open proximal state along an axial stroke C, to participate in defining a chamber,
- a second means, generally elongated, mounted axially in the first means, with an interposed lateral sealing component, so as to be axially slidable along the stroke C between the closed distal state and the open proximal state, arranged to comprise a transverse head at its proximal end portion which is adapted, in the closed distal state, to close the opening in a fluid-tight manner, to contain a space having a proximal wall formed by the adjacent head, a distal boundary, and a side passage opening, to comprise at its distal end portion an axially slidable actuating part, and to form a support for the accessory so that its active part is positioned within said space, to participate in defining a chamber,
- a chamber including said space and which, in the closed distal state, is closed off laterally by the first means and, where appropriate, is adapted to contain in a fluid-tight manner a liquid for preservation, adjustment, monitoring, or calibration of the accessory, and which, in the open proximal state, is freed of the first means and thus is able to be in communication with the inside by the side passage opening.

This device is such that
- the first means comprises a proximal end portion for fixed assembly by sliding, arranged so as to be assembled in a fixed and fluid-tight manner, with an interposed lateral sealing component, to a complementary fixed assembly part of the receptacle, by means of at least an axial sliding in the proximal direction,
- the transverse head has a peripheral lateral dimension and shape that fit with those of the inner surface of the first means, so as to be axially slidable within the first means in the proximal direction, from its distal opening to its proximal end portion, the head being fitted with a lateral sealing component such as a head seal,
- the second means is adapted for pre-assembly to the first means by an axial sliding in the proximal direction, the accordingly pre-assembled first means and second means thus forming a structural whole adapted for assembly to said complementary assembly part by sliding axially in the proximal direction.

According to some embodiments, in the closed distal state the head is located at or adjacent to the proximal opening of the first means, and/or the actuating part is located away from the distal end portion of the first means, in the distal direction, by a distance at least equal to the stroke C. In the open proximal state, the head is located away from the proximal opening of the first means, in the proximal direction, by a distance at least equal to the stroke C, and/or the actuating part is located at or adjacent to or near the distal end portion of the first means, in particular outside the first means.

According to some embodiments, the first means comprises, in particular consists of, a single first part, and/or the second means comprises, in particular consists of, a single second part, with mounted lateral sealing components.

According to one embodiment, the first means comprises a first part of generally tubular shape extending in the axial direction for a length that is greater than the stroke C, in particular substantially greater than the stroke C, having an outer surface of a peripheral lateral dimension and shape corresponding to those of the inner surface of said complementary assembly part so as to be suitable for mounting axially within said complementary assembly part, said first part having a lateral radial outward flange adapted to engage with an edge of said complementary assembly part to prevent axial movement in the proximal direction and/or a sealing component placed between the outer surface of said first part and the inner surface of said complementary assembly part, in particular a seal supported by the outer surface of said first part.

According to one embodiment, the second means comprises a second part of generally tubular shape extending in the axial direction for a length that is greater than that of the first means, in particular at least equal to that of the first means plus the stroke C, and more particularly for a length close to that of the first means plus the stroke C. In particular, the second means comprises a second part equipped at its distal end portion with a lateral radial outward flange adapted to engage with the edge of the distal end portion of the first means to prevent axial movement in the proximal direction, forming the actuating part where appropriate.

According to one embodiment, the second means is mounted axially within the first means with one or more interposed lateral sealing components in the form of one or more seals supported by the outer surface of the second means, in particular a distal sealing component and a proximal sealing component spaced from one another in the axial direction. In particular, the distance in the axial direction between the distal sealing component and the proximal sealing component is greater, in particular slightly greater, than the distance in the axial direction between the proximal sealing component and the head sealing component. In particular, the distance in the axial direction between the proximal sealing component and the head sealing component is close to or equal to the stroke C.

According to one embodiment, a channel for liquid is arranged in the second means, such as a borehole, extending axially, operatively associated with the accessory in particular for preservation, adjustment, monitoring, or calibration, having a proximal end opening into said space, respectively into said chamber, and a distal end opening which opens towards the distal end portion of the second means, arranged so that the channel is able to be extended distally beyond the second means, by an external connection component, such as comprising at least one tube. In particular, the connection device comprises at least two channels for respectively feeding and draining.

According to one embodiment, the first means and the second means are pre-assembled to form a structural whole in the closed distal state. In particular, the accessory is attached from the very start to the second means, in particular by overmolding the distal portion of the accessory, and/or the closed chamber is filled with a calibration liquid for the accessory.

A second aspect of the invention relates to an assembly for the measurement or monitoring of a parameter of a liquid contained inside a receptacle by means of a measurement or monitoring accessory of which the active proximal part is intended to be placed in communication with the inside of the receptacle by an opening in the receptacle, said assembly for measurement or monitoring comprising said accessory, a connection device as described, and, where appropriate, a calibration liquid for the accessory filling the closed chamber of said connection device in the closed distal state, said assembly for measurement or monitoring being ready for mounting onto a receptacle.

In an embodiment where the connection device is of the type having one or more channels, said assembly for measurement or monitoring also comprises, associated with the channel or with each of the channels by a fixed and communicating connection, the external connection component, such as comprising at least one tube, and, where appropriate, one or more components for connection, stopping flow, allowing flow, filtration, measurement, containment for the supply or collection of the liquid intended to pass through said external connection component and said associated channel.

In another embodiment, in which the connection device is of the type in which one or more channels are provided in the second means, said assembly for measurement or monitoring also comprises, associated with the channel or with each of the channels by a fixed and communicating connection, the external connection component, such as comprising at least one tube and one or more sampling components able to collect a sample of the receptacle contents trapped in the chamber after the connection device transitions from the open state to the closed state.

According to one embodiment, the accessory is a probe for measuring the pH of the contents contained within the inside of the receptacle.

A third aspect of the invention relates to an assembly with receptacle for biopharmaceutical applications with measurement or monitoring of a parameter of a liquid contained inside the receptacle, comprising: a receptacle, having a wall provided with an opening; and, attached in a rigid and fluid-tight manner to said wall around the opening, a complementary assembly part for fixed and fluid-tight assembly, adapted to cooperate with the proximal end portion for the fixed assembly of the first means of a connection device or of an assembly for measurement or monitoring as previously described.

According to one embodiment, the complementary assembly part for fixed and fluid-tight assembly has a generally tubular shape with a proximal end having an opening and a distal end having an opening, and a flange at the proximal end adapted for securing in a fixed and fluid-tight manner to the wall of the receptacle around its opening.

According to the embodiments, the receptacle 2 is either rigid and reusable or is flexible and disposable, such as a bag referred to as a 2D or 3D bag, and in the latter case, according to one embodiment, rigid external support means are provided for the receptacle, equipped with a passage for the connection device or for the assembly for measurement or monitoring.

A fourth aspect of the invention relates to a method for the pre-assembly of an assembly for measurement or monitoring of a parameter as described above, for its subsequent mounting onto a receptacle, which comprises the following successive steps:

means appropriate for constituting a connection device as described above are provided, a measurement or monitoring accessory is provided, the second means of the connection device and the accessory are arranged so the second means supports the accessory such that its active part is located within said space formed by the second means, the second means is slid axially in the proximal direction within the first means from its distal end opening, to the closed distal state.

According to some embodiments, in the distal closed state, the closed chamber is filled with a liquid for the preservation and/or calibration of the accessory, and the method is performed with no need for containment within a clean room.

A fifth aspect of the invention relates to a method for mounting an assembly with receptacle as described above, which comprises the following successive steps:
a receptacle empty of content is provided that is equipped, around an opening of a complementary assembly part, with a connection device (1),
an assembly for measurement or monitoring of a parameter as described above is provided,
the assembly for measurement or monitoring of a parameter is slid axially in the proximal direction within said complementary assembly part from its distal end opening, to the closed distal state.

According to one embodiment, the method for mounting an assembly with receptacle comprises a subsequent step of sterilizing the assembly with receptacle.

A sixth aspect of the invention relates to a method for utilizing an assembly for measurement or monitoring of a parameter as part of an assembly with receptacle, mounted as described above, which comprises the following sequence of steps:
as the chamber is empty, the second means of the connection device is slid axially in the proximal direction, from the closed distal state to the open proximal state,
the accessory is utilized.

According to one embodiment, the utilization method comprises at least one additional operation of preservation, adjustment, monitoring, or calibration of the accessory, in particular an initial operation before the receptacle is filled with its contents, a final operation after the receptacle is emptied of its contents, and, where appropriate, an operation after the receptacle is filled with its contents and before it is emptied of its contents, while the assembly for measurement or monitoring of a parameter and its connection device are in the closed distal state and the chamber is closed.

In particular, the invention allows storing, calibrating, and using a disposable probe under sterile or non-sterile conditions.

The invention is particularly applicable in the biopharmaceutical field, for example for applications related to mixing, for single-use bioreactors, and for temperature regulation.

We will now describe a particular embodiment of the invention with reference to the drawings, in which.

The device 1 is intended for the connection, to a receptacle 2 for biopharmaceutical use, of an accessory 3 adapted to be placed in communication with the inside 4 of the receptacle 2 and its contents, such as a fluid biopharmaceutical product as defined. Such a device 1 is an improvement of the device disclosed in WO 2009/071829, which is taken into account in the teachings.

The term "connected" is understood to mean that originally the receptacle 2 and the accessory 3 are completely separate, and that, by means of the device 1, the accessory 3 is attached and connected to the receptacle 2, and that a functional link can be established between the receptacle 2, and its contents, and the accessory 3.

"Assembly for measurement or monitoring" is understood to mean the assembled assembly 1+3, comprising the connection device 1 and the accessory 3 and, where appropriate, a calibration liquid for the accessory 3, filling the closed chamber 18 of said connection device 1 in the closed distal state. Such an assembly 1+3 for measurement or monitoring is ready for mounting onto a receptacle 2.

"Assembly with receptacle" or "operative container" are understood to mean a mounted assembly 1+2+3, comprising: a receptacle 2 for biopharmaceutical applications, with measurement or monitoring of a parameter of a liquid inside 4 the receptacle 2, the receptacle 2 having a wall 6 provided with an opening 7; and, rigidly attached in a fluid-tight manner to said wall 6 around the opening 7, a fixed and fluid-tight complementary assembly part 19 able to cooperate with a proximal end portion 32 for fixed assembly of a first means 15 (in this case a first part 15) of the connection device 1 or of an assembly 3+1 for measurement or monitoring. Such an assembly 1+2+3 with receptacle constitutes an operative container and is intended for the storage and/or processing of a biopharmaceutical product, hereinafter referred to as the contents.

Depending on which embodiments are considered, the receptacle 2 is rigid and reusable or is flexible and disposable such as a bag such as a 2D or 3D bag, as has been defined above.

According to one embodiment, such a 3D bag has a generally parallelepiped shape, particularly cubic or substantially cubic, with a peripheral wall 6 forming at least the bottom and side parts, and usually the upper part, so that the receptacle 2 is of the closed type, and one or more ports arranged in the wall that are appropriate for their purpose. In one embodiment corresponding to a large volume which exceeds 50 L and can reach 3000 L, the receptacle 2 is foldable.

With such a flexible receptacle 2, the operative container further includes rigid external support means. These means, whose existence is well-known, are not represented. In particular they may be a metal bin having solid or non-solid walls.

The wall 6 of the receptacle 2 is provided with an opening 7 for mounting, transversely to the wall 6, the connection device 1 and the accessory 3, so that the latter can be placed in communication with the inside 4 the receptacle 2 and in particular be placed in contact with the contents of the receptacle 2, even though the accessory 3 is located at least substantially outside 8 the receptacle 2.

What has just been described for the case of a 3D bag can be applied to a 2D bag and to a rigid receptacle 2.

The device 1 has a longitudinal axis 1a arranged at least substantially perpendicularly to the wall 6, as the accessory 3 usually does as well.

The inside 4 of the receptacle 2 is conventionally defined as the area internal to the receptacle 2, defined by the enclosing wall 6 and located on the side where most of the contents are located. The outside of the receptacle 8 is defined as the area lying on the other side of the enclosing wall 6.

The rigid outer support means for the receptacle 2, when provided, comprise a passage for the connection device 1, positioned facing or substantially facing the opening 7.

The term "accessory" does not mean that the designated object 3 is secondary or merely optional, but that the object 3 is complementary and in a close dependency with the receptacle 2 and the contents thereof, having a function which goes hand in hand with the function of the receptacle 2.

In the context of the invention, the accessory 3 is preferably disposable, as is the connection device 1.

In the illustrated embodiment, the accessory 3 is a probe comprising an active proximal part 9 able to measure, detect, monitor, record (subsequently measure) one or more relevant parameters relating to the contents of the receptacle 2, in particular such as pressure, pH, temperature, colorimetry, conductometry.

In general, the accessory 3 has an outer casing of more or less complex shape that is elongated, in particular rotationally symmetrical with a circular base, with the active proximal part 9 and a distal end portion 10. The distal end portion 10 may be associated with means such as an electrical conductor, a tube, etc.

In the embodiment shown, the accessory 3 is positioned centrally with respect to the axis 1a.

Figure 2:
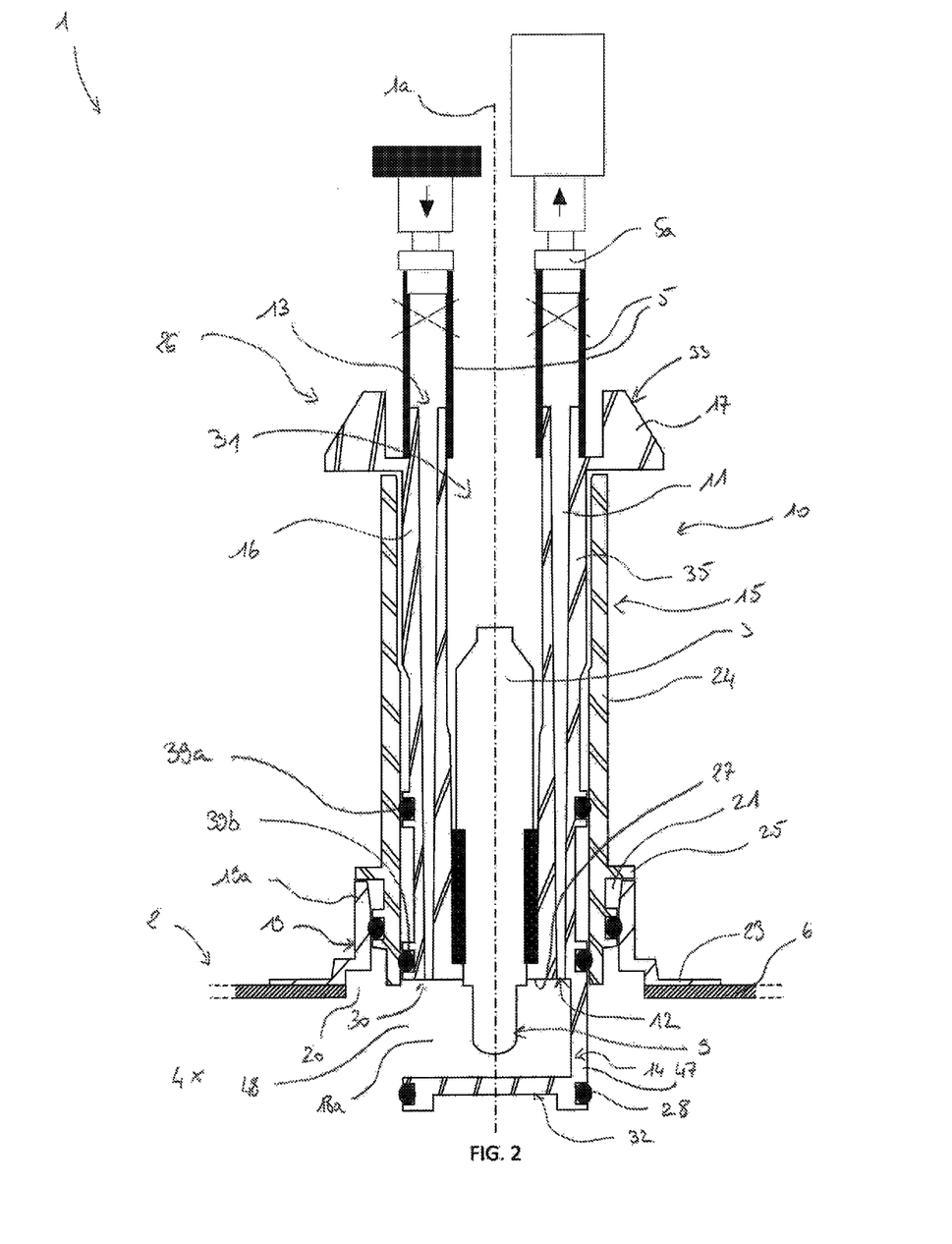
FIG. 2 is a view similar to FIG. 1, but in the open proximal state corresponding to a situation where the probe can be used.

The active part 9 of the accessory 3 is able, when appropriate or when desired, to be placed in communication with the inside 4 of the receptacle 2, and more specifically to be placed in contact with the contents of the receptacle 2, in order to carry out its measurement function. In this case it is arranged, as shown in FIG. 2, so that the active proximal part 9 is able to be introduced inside 4 the receptacle 2, passing through the opening 7 in the wall 6 in order to move beyond said wall where it is in close contact with the contents, in an area where the contents are homogeneous or at least sufficiently homogeneous, for the parameter in question, with the rest of the contents of the receptacle 2. The opening 7 is then preferably located at or near the bottom of the receptacle 2, meaning at a level lower than the level of the contents of the receptacle 2 even when the amount of the contents is low and the level is near the bottom of the receptacle 2.

In another embodiment, not shown, the active proximal part 9 of the accessory 3 is not, strictly speaking, introduced inside 4 the receptacle 2 but is brought to the wall 6 and in proximity to the opening 7 without insertion through it, although still in communication with the inside 4 of the receptacle 2. In another embodiment, not shown, the active proximal part 9 is brought into the opening 7, within the plane of the wall 6, so as to be in communication with the inside 4 of the receptacle 2.

In these various embodiments, situations, and positions, the active proximal part 9 of the accessory 3 (and the accessory 3 itself) is described as inserted into the receptacle 2 or into the inside 4 of the receptacle 2.

In other embodiments, which may be combined with the above embodiments, not just one but several accessories 3 such as probes are provided, either for measuring several parameters or at different locations, particularly different heights, in the receptacle 2.

In a second embodiment, not shown, the accessory 3 is a feed tube and/or a drain tube for the contents of the receptacle 2 or for one or more components thereof. This tube comprises an active proximal part 9 near the receptacle 2, consisting of a feed opening if the tube is or acts as a feed tube, or a drain opening if the tube is or acts as a drain tube, this opening being conventionally located at the free end of the tube. The active proximal part 9 of the tube is able, when necessary, to be placed in communication with the inside 4 of the receptacle 2, in order to fulfill its feed and/or drain function. The active proximal part 9 of the tube is then brought into the opening 7, within the plane of the wall 6, or is introduced inside 4 the receptacle 2, passing through the opening 7 in the wall 6, or is brought to the wall 6 and in proximity to the opening 7 without insertion through it. These various embodiments, situations, and positions correspond to what has been defined as the insertion of the active proximal part 9 into the receptacle 2 or into the inside 4 of the receptacle 2. When the accessory 3 is a feed tube and/or a drain tube, the opening 7 is positioned relative to the bottom of the receptacle 2 at the height appropriate for the purpose of the tube: at a level near the bottom of receptacle 2, or conversely at a level that is some distance from the bottom.

According to the embodiment represented, in the case where the accessory 3 is a pH probe, it is arranged that the connection device 1 and specifically a second means 16 (in this case a second part 16) provides a channel 11, and more particularly at least two channels 11 which are respectively feed and drain channels. Such a channel 11 for liquid, such as a borehole, extends axially and is operatively associated with the accessory 3, in particular for its preservation, adjustment, monitoring, or calibration. Such a channel 11 is positioned at or in proximity to the accessory 3 while being eccentric relative thereto. Such a channel 11 has a proximal end opening 12 into a space 18a of the connection device 1, respectively into the chamber 18, and a distal end opening 13 which opens toward the distal end portion 26 of the second means (second part) 16. The channel 11 is able to be extended distally, beyond the second means (second part) 16, by an external connection component 5, such as comprising at least one tube. In addition, there may be provided, associated with the channel 11 or with each of the channels 11, by a fixed and communicating connection, the external connection component 5, such as comprising at least one tube, and, where appropriate, one or more components 5a for connection (for example a Luer fitting), stopping flow (for example a clamp), allowing flow, filtration, measurement, containment for the supply or collection of the liquid intended to pass through said external connection component 5 and said associated channel 11.

More generally, it is also possible to use a sampling component 5a for recovering, by suction through the external connection component 5 or by any other similar process, a sample of the biopharmaceutical content trapped in the chamber after the connection device according to the invention transitions from the open state to the closed state.

The term "proximal" conventionally refers to what is relatively close, or closest, to the receptacle 2, particularly the inside 4. Conversely, the term "distal" refers to what is relatively far away from, or farther away from, the receptacle 2, particularly the inside 4. These terms are used to identify the component parts of the connection device 1, of the accessory 3, etc. It is understood, however, that the connection device 1 or the accessory 3 or the operative part 11 can be considered by itself, independently of the receptacle 2, before mounting onto the receptacle. These terms are also used to identify the location of the component parts of the device 1 of the accessory 3 relative to the receptacle 2, or to identify their position relative to said receptacle if this position is not fixed. Lastly, these qualifiers are conventionally used to distinguish the two states of the connection device 1, the accessory 3, the assembly 1+3 for measurement and monitoring, and the assembly 1+2+3 with receptacle.

Figure 1:
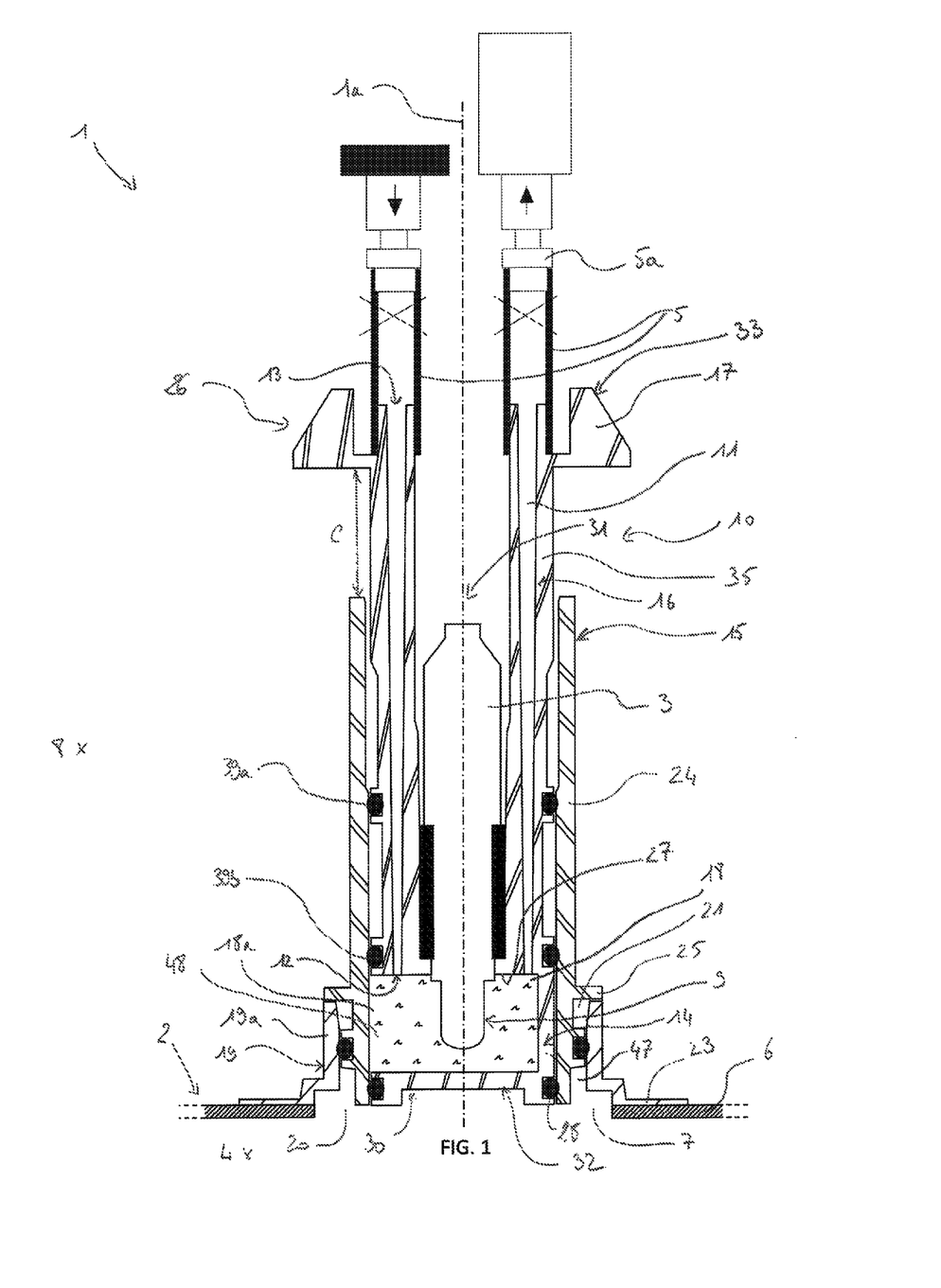
FIG. 1 is an axial cross-sectional view illustrating the connection device mounted on a container which is partially represented, with the accessory schematically represented as a probe, the connection device and the assembly for measurement or monitoring of a parameter being in the closed distal state corresponding to a storage and/or calibration situation.

Indeed, the connection device 1, the accessory 3 and specifically its active proximal part 9, the assembly 1+3 for measurement and monitoring, and the assembly 1+2+3 with receptacle can be found in one of two possible extreme states corresponding to two positions relative to the receptacle 2, corresponding to two states of being, functions, or possibilities for action. These states are understood to be when the connection device 1 and the accessory 3 are mounted on the receptacle 2. However, as above, it is understood that the connection device 1 or the accessory 3 can be considered by itself, independently of the receptacle 2 and before being mounted onto it; the two states can therefore be applied to them in such condition. These two states are illustrated by FIG. 1 and FIG. 2 respectively.

The two possible extreme states are a first state referred to as distal (FIG. 1) and a second state referred to as proximal (FIG. 2). The qualifiers "first" and "second" are used to express that the initial state is the closed distal state. The distal state is a closed state and the proximal state is an open state.

In the closed distal state (FIG. 1), the active proximal part 9 of the accessory 3 is completely separated, in a fluid-tight manner, from the inside 4 of the receptacle 2, by a head 14 forming a barrier which is part of the connection device 1 and more specifically its second means (second part) 16. Specifically, in the closed distal state, the head 14 is located at or adjacent to the proximal end opening 30 of the first means 15, and an actuating part 17 at the distal end portion 26 of the second means (second part) 16, formed by a lateral radial outward flange, is located at a distance away from the end of the distal end portion 33 of the first means (first part) 15, in the distal direction, by a distance at least equal to the stroke C.

In the open proximal state (FIG. 2), the active proximal part 9 of the accessory 3 is in communication with the inside 4 and inserted into the receptacle 2, so as to be in contact with the contents of the receptacle 2, which allows the accessory 3 to perform its function, especially in the case of a probe 3, of measuring or monitoring a parameter of the contents of the receptacle 2. The head 14 then protects the active proximal part 9 against, for example, solids moving about inside 4 the receptacle 2 or components in motion such as the parts of a mixer. Specifically, in the open proximal state, the head 14 is located away from the proximal end portion 32 of the first means (first part) 15, in the proximal direction, by a distance at least equal to the stroke C, and the actuating part 17 is located at, or adjacent to, or near, the distal end portion 31 of the first means (first part) 15, in particular outside of the first means (first part) 15, so as to be able to engage with the edge of the distal end portion 33 of the first means 15 to prevent axial movement in the proximal direction.

In the embodiment shown, corresponding to the case where the accessory 3 is a probe 3, the closed distal state (FIG. 1) is typically the state corresponding to storage or calibration, while the open proximal state (FIG. 2) is typically the state for measuring a parameter for the contents of the receptacle 2, by means of the accessory 3 utilized for this purpose.

In the case (not shown) where the accessory 3 is a tube, the closed distal state is typically the state corresponding to storage or disuse of the feed or drain function of the tube, while the open proximal state is the state for using the feed or drain function of the tube.

The connection device 1 comprises a first means 15 (a first part 15) and a second means 16 (a second part 16). The first means 15 and the second means 16 are assembled together. The accessory 3, and where appropriate the channel 11, are provided in the second means 16. The connection device 1 further comprises a space 18a and a chamber 18.

The first means (first part) 15 has several functions:
It ensures that the connection device 1 is rigidly attached to the receptacle 2, by means of the fixed assembly part 19, which is part of the receptacle 2.
It defines a passageway between the inside 4 and the outside 8 of the receptacle 2.
For the second means (second part) 16, it serves as a support that guides the axial sliding along the axis 1a, along a given stroke C having two ends of travel that respectively correspond to the first closed distal state and the second open proximal state.
It participates in defining the chamber 18.

The second means (second part) 16 also has several functions:
It forms a movable element sliding axially along the axis 1a in a stroke C having two ends of travel that respectively correspond to the first closed state distal and the second open proximal state.
It serves as support for the accessory 3, and where appropriate the channel 11 such as a borehole.
In the closed distal state, it seals the opening 7 by means of the head 14, by closing in a fluid-tight manner the proximal end opening 30 of the first element 15, thereby forming a barrier preventing access to the inside 4 of the receptacle 2 and preventing communication between the accessory 3 and the inside 4 of the receptacle 2.
In the open proximal state, it protects the active proximal part 9 of the accessory by means of the head 14, especially when actually inserted inside 4 the receptacle 2.
It also participates in defining the chamber 18.

In the embodiment illustrated, the first means 15 comprises and more specifically consists of one first part 15, and the second means 16 comprises and more specifically consists of one second part 16, with intervening and mounted lateral sealing components 39a, 39b. Of course, the invention extends to other embodiments having multiple parts secured together, this embodiment being considered equivalent. The parts 15 and 16 are for example made of or are based on plastic or contain plastic or certain portions are made of silicone.

The first means 15 (first part 15), the second means 16 (second part 16), and the fluid-tight complementary fixed assembly part 19 are tubular in shape to allow mounting them as indicated. If these three parts 15, 16 and 19 are intended to be moved relative to each other by axial sliding, they are cylindrical or prismatic in shape. If they are intended to be moved relative to each other by axial sliding and by rotation about the axis, they are in the form of circular cylinders.

The fluid-tight complementary fixed assembly part 19 will now be more specifically described. The complementary assembly part 19 can be considered as part of the receptacle 2, attaching in a fluid-tight seal around the receptacle opening 7. The complementary assembly part 19 is not itself part of the connection device 1, although it is essential to the connection device 1.

The complementary assembly part 19, rigid and in this case a single unit, has a generally tubular shape of axis 1a, with a cylindrical or prismatic side wall 19a, having a proximal end with a proximal end opening 20 and a distal end with a distal end opening 21, and a transverse annular proximal end flange 23, extending laterally outward with sufficient radial extension for securing it in a fixed and fluid-tight manner to the wall 6 of the receptacle 2 around the receptacle opening 7, for example by ultrasonic welding, adhesive bonding, or similar. The diameter of the tubular side wall 19a corresponds to the diameter of the opening 7 and to the diameter of the first means (first part) 15, so that the first means (first part) 15 can be fitted into the complementary assembly part 19. The axial length of the complementary assembly part 19 and therefore of the tubular side wall 19a is sufficient for holding the first means (first part) 15 and therefore the connection device 1. For example, the axial length of the complementary assembly part 19 and of the tubular side wall 19a can be around that of the stroke C. Due to its tubular shape with its two proximal and distal end openings 20, 21, the complementary assembly part 19 forms a passageway for the contents of the receptacle 2 from the inside 4 and permits the passage of the connection device 1 at the distal end opening 21 and at the proximal end opening 20.

The first part 15 forming the first means 15 will now be more specifically described.

The first part 15, which is rigid, is generally tubular with axis 1a, comprising a tubular wall 24, a proximal end portion 32 having a proximal end opening 30, and a distal end portion 33 having a distal end opening 31, and extends axially for a greater length than the stroke C, in particular substantially larger than the stroke C, for example ranging from three to six times the stroke C, although these values are not limiting.

The outer surface of the tubular wall 24 has a shape and peripheral lateral dimension corresponding to those of the inner surface of said complementary assembly part 19. The first part 15 can thus be mounted axially within the complementary assembly part 19. The inner surface of the tubular wall 24 corresponds to, aside from the necessary clearance to allow for the presence of the interposed sealing components 39a, 39b, the outer diameter of the second part 16.

The first part 15 has a lateral radial outward flange 25 adapted to engage with the edge of the distal end 21 of the complementary assembly part 19 to prevent axial movement in the proximal direction so that, as shown, the proximal end portion 32 of the first part 15 is in line or more or less in line with the flange 23 of the complementary assembly part 19.

A lateral sealing component 22 is positioned between the outer surface of the first part 15 and the inner surface of the complementary assembly part 19. This sealing component 22 is in particular an O-ring of silicone or other equivalent material, supported by the outer surface of said first part 15 in a groove provided for this purpose.

Thus, the first part 15 constitutes a passageway between the inside 4 and the outside 8 of the receptacle 2. Furthermore, the first part 15 comprises, towards its proximal end portion 32, an end portion slid for its fixed assembly, which can be assembled in a fixed and fluid-tight manner, with a lateral sealing component 22 positioned between, to the complementary fixed assembly portion 19 of the receptacle 2. This assembly is achieved by at least an axial slide in the proximal direction. Also, the inner surface of the tubular wall 24 of the first part 15 forms a guide to support the axial sliding of the second part 16 between the closed distal state and the open proximal state, the distal end opening 31 allowing the mounting of the second part 16 within the first part 15, and the proximal end opening 30 allowing the second part 16 and the accessory 3 to pass through and emerge inside 4. And finally, the first part 15 participates in defining the chamber 18. In the embodiment represented, the distal end portion 33 also acts as a stop for the actuating part 17 of the second part 16 in the open proximal state.

The first part 15 and the complementary assembly part 19 are mutually arranged so that the complementary assembly part 19 provides sufficient retention of the first part 15. Such retention may be the result of forced insertion. It may also result from the cooperation of complementary elements provided on the first part 15 and on the complementary assembly part 19, such as a helical-type kinematic coupling such as a relative axial pivoting imparted to the first part 15 causing cooperative axial sliding of the complementary assembly part 19. Such a helical-type kinematic coupling may, in particular, comprise a lateral pin on one part engaging with a helical groove in the other part.

The second part 16 forming the second means 16 will now be specifically described.

The second part 16, which is rigid and generally elongated in shape, is mounted within the first part 15, axially with respect to axis 1a, with lateral sealing components 39a, 39b positioned between. The second part 16 is thus adapted for sliding axially, relative to the first part 15 and to what is fixedly connected such as the complementary assembly part 19 and the receptacle 2, along the stroke C between the closed distal state and the open proximal state.

The second part 16 is generally tubular and extends in the axial direction for a length greater than the length of the first part 15, in particular at least equal to that of the first part plus the stroke C, and more particularly for a length close to that of the first part 15 plus the stroke C, as in the embodiment shown.

The second part 16 comprises a body 35 and, at its proximal end portion, the transversely arranged head 14. A part 47 acting as a spacer connects the body 35 to the head 14, the latter having a fixed position relative to the body 35. The term "spacer" is not in itself limiting and refers to the fact that the part 47 is a sufficiently rigid support extending axially and keeping the head 14 fixed relative to the body 35. This spacer 47 is arranged to provide a side passage opening 48 allowing the contents of the receptacle 2 to pass through.

The spacer 47 may be present in various equivalent forms: for example as several parts such as rods distanced from one another, or as a single part such as a perforated sleeve. The side passage opening 48 is, as in the embodiment shown, composed of several parts and is defined by the shape given to the spacer 47.

The axial length of the spacer 47 is adapted to allow an active proximal part 9 to be in contact with the contents of the receptacle 2.

A space 18a is formed beyond the body 35 in the proximal direction, between the proximal boundary of the body 35 and the head 14. This space 18a has a proximal wall formed by the adjacent head 14, a distal boundary 27 which is the proximal boundary of the body 35, and the side passage opening 48.

The body of the second part 16 comprises the actuating part 17 on its distal end portion 26, which when actuated, for example manually, axially slides the second part 16 within the first part 15.

The body of the second part 16 forms a support for the accessory 3 so that its active proximal part 9 is located within the space 18a. In the embodiment shown, the accessory 3 is attached from the very first to the second part 16, in particular by overmolding the distal portion 10 of the accessory 3.

The head 14 has two functions:
In the closed distal state, the head 14 seals shut the opening 7 and the connection device 1 on the proximal side, by forming a barrier which prevents access to the inside 4 of the receptacle 2 and closes off communication between the accessory 3 and the inside 4 of the receptacle 2.
In the open proximal state, the head 14 participates in protecting the active proximal part 9, especially if it is inserted through the opening 7 into the inside 4 of the receptacle 2.

The head 14 is present in the general form of a solid transverse wall. Its peripheral lateral dimension and shape fit with those of the inner surface of the first part 15 so as to allow inserting it axially into the first part 15 in the proximal direction, from its distal end opening 31, and then sliding it axially into the first part 15 in the proximal direction, from its distal end opening 31 all the way to its proximal end opening 30.

The head 14 is fitted on its exposed lateral edge with a lateral sealing component 28, such as an O-ring type seal, of silicone or other equivalent material, engaging in a fluid-tight manner with the inner surface of the tubular wall 14 of the first part toward the proximal end portion 32, when in the closed distal state. The head 14 with its seal 28 is therefore adjusted so as to cooperate in a fluid-tight manner in the proximal end opening 30 or in the proximal end portion 32 of the first part 15.

With the structural arrangements indicated, the second part 16 is adapted for pre-assembly to the first part 15 with axial sliding in the proximal direction. Thus, the first part 15 (more generally the first means) and second part 16 (more generally the second means) pre-assembled in this manner form a structural whole adapted for assembly to said complementary assembly part 19 of the receptacle 2, by sliding axially in the proximal direction.

The second part 16 and the first part 15 are mutually arranged so as to cooperate, the second part 16 being within the first part 15 and able to at least slide relative to it. Such an arrangement can result from a slidable assembly. It can also result from a slidable and pivotable assembly, with the cooperation of complementary elements provided on the first part 15 and on the second part 16, such as a helical-type kinematic coupling such as a relative axial pivoting imparted to the second part 16 causing it to slide axially along the first part 15. Such a helical-type kinematic coupling may, in particular, comprise a lateral pin on the one part cooperating with a helical groove in the other part.

The second part 16 is axially mounted within the first part 15, in this case with two interposed lateral sealing components 39a, 39b in the form of one or more seals supported by the outer surface of the second part 16. The distal sealing component 39a and the proximal sealing component 39b are spaced apart from each other in the axial direction.

The distance in the axial direction between the distal sealing component 39a and the proximal sealing component 39b is greater, in particular slightly greater, than the distance in the axial direction between the proximal sealing component 39b and the head sealing component 28; these may be spaced apart axially by a distance close to or equal to the stroke C.

The head seal 18 is fluid-tight to the biopharmaceutical fluid.

The proximal seal 39b is fluid-tight to the biopharmaceutical fluid and to potential contaminants of external origin.

The distal seal 39a is fluid-tight to potential contaminants of external origin.

All the above structural arrangements allow combining the following: good guidance due to providing a sufficient support distance, good sliding, a good seal, and prevention of contamination by potential contaminants of external origin as the second part 16 slides back and forth. In addition, the first means (first part) 15 and the second means (second part 16) can be pre-assembled to form a structural whole in the closed distal state. This structural whole can include the accessory 3 attached to the second part 16, in particular by overmolding the distal portion 10, and a calibration liquid for the accessory 3 filling the chamber 18. Moreover, the structural arrangements described above allow actuating the valve multiple times in the sequence closed state→open state→closed state→open state—which can be particularly useful when recalibrating the accessory 3—while guaranteeing non-contamination of the biopharmaceutical contents of the receptacle 2 by microorganisms as the connection device 1 is manipulated.

The connection device 1 comprises the chamber 18, which includes a space 18a. In the closed distal state, the chamber 18 is closed off laterally by the tubular wall 24 of the first part 15, which covers the opening of the side passage opening 48 and thus seals it. In this situation, the chamber 18 is fluid-tight and can contain a liquid for preserving, adjusting, verifying, or calibrating the accessory 3. In the open proximal state, the first part 15 is clear of the chamber 18 and the latter is therefore open via the side passage opening 48. It is then able to be placed in communication with the inside 4 via the side passage opening 48, and the same is therefore true for the active proximal part 9 of the accessory 3.

Depending on the application and on requirements, the chamber 18 may be sterile or non-sterile, wet or dry, according to the accessory 3. For example, a pH probe requires a humid environment. This humid environment is obtained by the presence in the chamber 18 of a specific liquid injected at the time of storage and referred to for this reason as "storage liquid."

If the accessory 3 requires a dry environment rather than a humid environment, as is the case when the accessory 3 is a tube, such a storage liquid is not provided.

In the case where the accessory 3 is a probe 3, one function of the chamber 18 is to conduct a calibration of the accessory. A calibration liquid is placed in the chamber 18 for this purpose.

The assembly (1+3) for measurement or monitoring of a parameter of a liquid located inside 4 the receptacle 2 comprises the connection device 1 and the accessory 3, and, where appropriate, the calibration fluid for the accessory 3 which fills the closed chamber 18, and, where appropriate, an external connection component 5 and one or more components 5a as previously described. Such an assembly 1+3 is ready for mounting onto the receptacle 2.

The assembly (1+2+3) with receptacle for biopharmaceutical application with measurement or monitoring of a parameter of a liquid located inside 4 the receptacle 2 comprises the receptacle 2, with its wall 6 provided with an opening 7, and, rigidly attached in a fluid-tight manner, the complementary assembly part 19 which cooperates with the connection device 1.

An assembly 3+1 for measurement or monitoring can be assembled before being mounted onto the complementary part 19 of the receptacle 2, which is why the term "pre-assembly" is used.

The method for pre-assembly is characterized by the following sequence of steps, once the means for constituting a connection device 1 and a measurement or monitoring accessory 3 have been provided:
  the second means 16 of the connection device 1 and the accessory 3 are arranged so the second means 16 supports the accessory 3 such that its active part 9 is located within the space 18a,
  then the second means 16 is slid axially in the proximal direction within the first means 15 from its distal end opening 31, to the closed distal state.

According to one embodiment, in the closed distal state, the closed chamber 18 is filled with a calibration liquid for the accessory 3.

Given the structural characteristics of the connection device 1, the pre-assembly which has just been described can be achieved with no need for containment within a clean room.

To mount an assembly 1+2+3 with receptacle, the following succession of steps are performed, once a receptacle 2 empty of content and equipped with the complementary assembly part 19 and an assembly 1+2 for measurement or monitoring have been provided: the assembly for measurement or monitoring 1+2 is slid axially in the proximal direction within the complementary assembly part 19 from its distal end opening 21, to the closed distal state. For biopharmaceutical applications, there is a further step of sterilizing the complete assembly 1+2+3 with receptacle, for example by gamma radiation, although this embodiment is not limiting.

To utilize such an assembly 1+3 for measurement or monitoring as part of an assembly 1+2+3 with receptacle, the following sequence of steps is performed:

the chamber 18 being empty, the second means 16 of the connection device 1 is slid axially in the proximal direction from the closed distal state to the open proximal state, then the accessory 3 is utilized.

In one typical embodiment, when the accessory 3 is a sensor such as a pH probe, the method comprises at least one additional operation of preservation, adjustment, monitoring, or, more typically, calibration of the accessory 3. Such an operation is an initial operation before the receptacle 2 is filled with its contents, a final operation after the receptacle 2 is emptied of its contents, and, where appropriate, an operation after the receptacle 2 is filled with its contents and before it is emptied of its contents. Such an operation is performed while the assembly 1+3 for measurement or monitoring and its connection device 1 are in the closed distal state and the chamber 18 is closed in a fluid-tight seal.

The invention claimed is:

1. Device (1) for the fluid-tight connection to a receptacle (2) of an accessory (3) of which the active proximal part (9) is intended to be placed in communication with the inside (4) of the receptacle (2) by an opening (7) in the receptacle (2), the device (1) having an axis (1a) and comprising:

a first means (15) of generally tubular shape with a proximal end opening (30) and a distal end opening (31), arranged to ensure the attachment of the device (1) to the receptacle (2), to define a passageway between the inside (4) and the outside (8) of the receptacle (2), to form a support that guides the axial sliding of a second means (16) between a closed distal state and an open proximal state along an axial stroke C, to participate in defining a chamber (18), a second means (16), generally elongated, mounted axially in the first means (15), with an interposed lateral sealing component (39a, 39b), so as to be axially slidable along the stroke C between the closed distal state and the open proximal state, arranged to comprise a transverse head (14) at its proximal end portion which is adapted, in the closed distal state, to close the opening (7) in a fluid-tight manner, to contain a space (18a) having a proximal wall formed by the adjacent head (14), a distal boundary (27), and a side passage opening (48), to comprise at its distal end portion an axially slidable actuating part (17), and to form a support for the accessory (3) so that its active part (9) is positioned within said space (18a), to participate in defining a chamber (18), a chamber (18) including said space (18a) and which, in the closed distal state, is closed off laterally by the first means (15) and, where appropriate, is adapted to contain in a fluid-tight manner a liquid for preservation, adjustment, monitoring, or calibration of the accessory (3), and which, in the open proximal state, is freed of the first means (15) and is thus able to be in communication with the inside (4) by the side passage opening (48), characterized in that the first means (15) comprises a proximal end portion (32) for fixed assembly by sliding, arranged so as to be assembled in a fixed and fluid-tight manner, with an interposed lateral sealing component (22), to a complementary fixed assembly part (19) of the receptacle (2), by means of at least an axial sliding in the proximal direction, the transverse head (14) has a peripheral lateral dimension and shape that fit with those of the inner surface of the first means (15), so as to be axially slidable within the first means (15) in the proximal direction, from its distal opening (31) to its proximal end portion (32), the head (14) being fitted with a lateral sealing component (28) such as a head seal, the second means (16) is adapted for pre-assembly to the first means (15) by an axial sliding in the proximal direction, the accordingly pre-assembled first means (15) and second means (16) forming a structural whole adapted for assembly to said complementary assembly part (19) by sliding axially in the proximal direction.

2. Connection device (1) according to claim 1, wherein, in the closed distal state, the head (14) is located at or adjacent to the proximal opening (30) of the first means (15), and/or the actuating part (17) is located away from the distal end portion (33) of the first means (15), in the distal direction, by a distance at least equal to the stroke C.

3. Connection device (1) according to claim 1, wherein, in the open proximal state, the head (14) is located away from the proximal opening (30) of the first means (15), in the proximal direction, by a distance at least equal to the stroke C, and/or the actuating part (17) is located at or adjacent to or near the distal end portion (33) of the first means (15), in particular outside the first means (15).

4. Connection device (1) according to claim 1, wherein the first means (15) comprises, in particular consists of, a single first part (15), and/or the second means (16) comprises, in particular consists of, a single second part (16), with mounted lateral sealing components (39a, 39b).

5. Connection device (1) according to claim 1, wherein the first means (15) comprises a first part (15) of generally tubular shape extending in the axial direction for a length that is greater than the stroke C, in particular substantially greater than the stroke C, having an outer surface of a peripheral lateral dimension and shape corresponding to those of the inner surface of said complementary assembly part so as to be suitable for mounting axially within said complementary assembly part (19), said first part (15) having a lateral radial outward flange (25) adapted to engage with an edge (21) of said complementary assembly part (19) to prevent axial movement in the proximal direction and/or a sealing component (22) placed between the outer surface of said first part (15) and the inner surface of said complementary assembly part (19), in particular a seal (22) supported by the outer surface of said first part (15).

6. Connection device (1) according to claim 1, wherein the second means (16) comprises a second part (16) of generally tubular shape extending in the axial direction for a length that is greater than that of the first means (15), in particular at least equal to that of the first means (15) plus the stroke C, more particularly for a length close to that of the first means (15) plus the stroke C.

7. Connection device (1) according to claim 6, wherein the second means (16) comprises a second part (16) equipped at its distal end portion (26) with a lateral radial outward flange (17) adapted to engage with the edge of the distal end portion (33) of the first means (15) to prevent axial movement in the proximal direction, forming the actuating part (17) where appropriate.

8. Connection device (1) according to claim 1, wherein the second means (16) is mounted axially within the first means (15) with one or more interposed lateral sealing components (39a, 39b) in the form of one or more seals supported by the outer surface of the second means (16).

9. Connection device (1) according to claim 8, characterized by a distal sealing component (39a) and a proximal sealing component (39b) spaced apart from one another in the axial direction.

10. Connection device (1) according to claim 9, wherein the distance in the axial direction between the distal sealing component (39a) and the proximal sealing component (39b) is greater, in particular slightly greater, than the distance in the axial direction between the proximal sealing component (39b) and the head sealing component (28).

11. Connection device (1) according to claim 9, wherein the distance in the axial direction between the proximal sealing component (39b) and the head sealing component (28) is close to or equal to the stroke C.

12. Connection device (1) according to claim 1, wherein a channel (11) for liquid is arranged in the second means (16), such as a bore hole, extending axially, operatively associated with the accessory (3) in particular for preservation, adjustment, monitoring, or calibration, having a proximal end opening (12) into said space (18a), respectively into said chamber (18), and a distal end opening (13) which opens towards the distal end portion (26) of the second means (16), arranged so that the channel is able to be extended distally beyond the second means (16), by an external connection component (5), such as comprising at least one tube.

13. Connection device (1) according to claim 12, comprising at least two channels (11) for respectively feeding and draining.

14. Connection device (1) according to claim 1, wherein the first means (15) and the second means (16) are pre-assembled to form a structural whole in the closed distal state.

15. Connection device (1) according to claim 14, wherein the accessory (3) is attached from the very start to the second means (16), in particular by overmolding the distal portion (10) of the accessory (3), and/or the closed chamber (18) is filled with a calibration liquid for the accessory (3).

16. Assembly (1+3) for the measurement or monitoring of a parameter of a liquid contained inside (4) a receptacle (2) by means of a measurement or monitoring accessory (3) of which the active proximal part (9) is intended to be placed in communication with the inside (4) of the receptacle (2) by an opening (7) in the receptacle (2), said assembly (1+3) for measurement or monitoring comprising said accessory (3), a device (1) for the connection of said accessory (3) to the receptacle (2) according to claim 1, and, where appropriate, a calibration liquid for the accessory (3) filling the closed chamber (18) of said connection device (1) in the closed distal state, said assembly for measurement or monitoring (1+3) being ready for mounting onto a receptacle (2).

17. Assembly (1+3) for measurement or monitoring according to claim 16, wherein the connection device (1) is of the type in which one or more channels (11) are provided in the second means (16), characterized by the fact that it also comprises, associated with the channel (11) or with each of the channels (11) by a fixed and communicating connection, the external connection component (5), such as comprising at least one tube, and, where appropriate, one or more components (5a) for connection, stopping flow, allowing flow, filtration, measurement, containment for the supply or collection of the liquid intended to pass through said external connection component and said associated channel.

18. Assembly (1+3) for measurement or monitoring according to claim 16, wherein the connection device (1) is of the type in which one or more channels (11) are provided in the second means (16), characterized in that said assembly also comprises, associated with the channel (11) or with each of the channels (11) by a fixed and communicating connection, the external connection component (5), such as comprising at least one tube and one or more sampling components (5a) able to collect a sample of the receptacle (2) contents trapped in the chamber after the connection device (1) transitions from the open state to the closed state.

19. Assembly (1+3) for measurement or monitoring according to claim 16, wherein the accessory (3) is a probe for measuring the pH of the contents contained within the inside (4) of the receptacle (2).

20. Method for mounting an assembly (1+2+3) with receptacle according to claim 19, characterized by the following successive steps:
   a receptacle (2) empty of content is provided that is equipped, around an opening (7) of a complementary assembly part (19), with a connection device (1),
   an assembly (1+3) for measurement or monitoring of a parameter is provided,
   the assembly (1+3) for measurement or monitoring of a parameter is slid axially in the proximal direction within said complementary assembly part (19) from its distal end opening (31), to the closed distal state.

21. Method for mounting an assembly with receptacle according to claim 20, comprising a subsequent step of sterilizing the assembly (1+2+3) with receptacle.

22. Method for utilizing an assembly (1+3) for measurement or monitoring of a parameter as part of an assembly (1+2+3) with receptacle, mounted according to claim 19, characterized by the following successive steps:
   as the chamber (18) is empty, the second means (16) of the connection device (1) is slid axially in the proximal direction, from the closed distal state to the open proximal state,
   the accessory (3) is utilized.

23. Utilization method according to claim 22, comprising at least one additional operation of preservation, adjustment, monitoring, or calibration of the accessory (3), in particular an initial operation before the receptacle (2) is filled with its contents, a final operation after the receptacle (2) is emptied of its contents, and, where appropriate, an operation after the receptacle (2) is filled with its contents and before it is emptied of its contents, while the assembly for measurement or monitoring of a parameter and its connection device (1) are in the closed distal state and the chamber (18) is closed in a fluid-tight seal.

24. Assembly (1+2+3) with receptacle for biopharmaceutical applications with measurement or monitoring of a parameter of a liquid contained inside (4) the receptacle (2), comprising: a receptacle (2), having a wall (6) provided with an opening (7); and, attached in a rigid and fluid-tight manner to said wall (6) around the opening (7), a complementary assembly part (19) for fixed and fluid-tight assembly, adapted to cooperate with the proximal end portion (30) for the fixed assembly of the first means (15) of a connection device (1) according to claim 1.

25. Assembly (1+2+3) with receptacle according to claim 24, wherein the complementary assembly part (19) for fixed and fluid-tight assembly has a generally tubular shape having a side wall (19a) with a proximal end having an opening (20) and a distal end having an opening (21), and a flange (23) at the proximal end adapted for securing in a fixed and fluid-tight manner to the wall (6) of the receptacle (2) around its opening (7).

26. Assembly (1+2+3) with receptacle according to claim 24, wherein the receptacle (2) is either rigid and reusable or is flexible and disposable, such as a bag referred to as a 2D or 3D bag.

27. Assembly (1+2+3) with receptacle according to claim 26, wherein the receptacle (2) is flexible, characterized by rigid external support means being provided for the receptacle (2), equipped with a passage for the connection device (1) or for the assembly for measurement or monitoring.

28. Method for the pre-assembly of an assembly (1+3) for measurement or monitoring of a parameter, for its subsequent mounting onto a receptacle (2), characterized by the following successive steps:
- means appropriate for constituting a connection device (1) according to claim 1 are provided,
- a measurement or monitoring accessory (3) is provided,
- the second means (16) of the connection device (1) and the accessory (3) are arranged so the second means (16) supports the accessory (3) such that its active part (9) is located within said space (18a) formed by the second means (16),
- the second means (16) is slid axially in the proximal direction within the first means (15) from its distal end opening (31), to the closed distal state.

29. Pre-assembly method according to claim 28, wherein, in the closed distal state, the closed chamber (18) is filled with a liquid for the preservation and/or calibration of the accessory (3).

30. Pre-assembly method according to claim 28, characterized by its being carried out with no need for containment within a clean room.

* * * * *